United States Patent
Murakami et al.

(10) Patent No.: US 10,980,715 B2
(45) Date of Patent: Apr. 20, 2021

(54) GEL COMPOSITION, COSMETIC, AND METHOD FOR PRODUCING GEL COMPOSITION

(71) Applicant: SUMITOMO SEIKA CHEMICALS CO., LTD., Hyogo (JP)

(72) Inventors: Ryosuke Murakami, Himeji (JP); Shingo Izawa, Himeji (JP); Satoshi Nishiguchi, Himeji (JP); Miyu Ikeda, Himeji (JP); Rie Nakashima, Himeji (JP)

(73) Assignee: SUMITOMO SEIKA CHEMICALS CO., LTD., Hyogo (JP)

(*) Notice: Subject to any disclaimer, the term of this patent is extended or adjusted under 35 U.S.C. 154(b) by 122 days.

(21) Appl. No.: 16/088,759

(22) PCT Filed: Mar. 24, 2017

(86) PCT No.: PCT/JP2017/011954
§ 371 (c)(1),
(2) Date: Sep. 26, 2018

(87) PCT Pub. No.: WO2017/170201
PCT Pub. Date: Oct. 5, 2017

(65) Prior Publication Data
US 2020/0129387 A1    Apr. 30, 2020

(30) Foreign Application Priority Data

Mar. 31, 2016 (JP) ............................. JP2016-072397
Jun. 9, 2016 (JP) ............................. JP2016-115204

(51) Int. Cl.
| | |
|---|---|
| A61K 8/04 | (2006.01) |
| A61K 8/46 | (2006.01) |
| A61K 8/81 | (2006.01) |
| A61Q 5/02 | (2006.01) |
| A61Q 19/10 | (2006.01) |
| C08F 220/06 | (2006.01) |

(52) U.S. Cl.
CPC ............. *A61K 8/042* (2013.01); *A61K 8/463* (2013.01); *A61K 8/8152* (2013.01); *A61Q 5/02* (2013.01); *A61Q 19/10* (2013.01); *C08F 220/06* (2013.01); *A61K 2800/48* (2013.01)

(58) Field of Classification Search
CPC ...... A61K 8/042; A61K 8/8152; A61K 8/463; A61K 2800/48; A61Q 19/10; A61Q 5/02; C08F 220/06
See application file for complete search history.

(56) References Cited

U.S. PATENT DOCUMENTS

| | | | |
|---|---|---|---|
| 3,915,921 A | 10/1975 | Schlatzer, Jr. | |
| 3,940,351 A | 2/1976 | Schlatzer, Jr. | |
| 4,419,502 A * | 12/1983 | Sehm | C08F 22/02 526/209 |
| 4,509,949 A | 4/1985 | Huang et al. | |
| 5,004,598 A | 4/1991 | Lockhead et al. | |
| 5,342,911 A | 8/1994 | Bresciani | |
| 5,985,793 A * | 11/1999 | Sandbrink | A01N 43/40 504/363 |
| 2009/0227751 A1 | 9/2009 | Yoskinaka et al. | |
| 2010/0267845 A1 | 10/2010 | Yoskinaka et al. | |
| 2015/0157549 A1 | 6/2015 | Murakami et al. | |
| 2016/0045424 A1 | 2/2016 | Schwab et al. | |

FOREIGN PATENT DOCUMENTS

| | | |
|---|---|---|
| JP | S516190 A | 1/1976 |
| JP | S59232107 | 12/1984 |
| JP | 2009-084502 A | 4/2009 |
| JP | 2010-235833 A | 10/2010 |
| JP | 2011-213676 A | 10/2011 |
| JP | 2015 224240 A | 12/2015 |
| WO | WO 2007/055354 A1 | 5/2007 |
| WO | WO 2009/084469 A1 | 7/2009 |
| WO | WO 2014/021434 A1 | 2/2014 |

OTHER PUBLICATIONS

Sergent et al, Reactive & Functional Polymers p. 962, Feb. 21 (Year: 2012).*
International Search Report for International Publication PCT/JP2017/011954, dated May 30, 2017 (in 2 pages).
Supplemental European Search Report issued for Counterpart European Patent Application No. 17774737.5 (dated Sep. 16, 2019).
Sumitomo Seika Technical Data Sheet 2009 "AQUPEC SER W-150C (CT-1), W-300C (CT-1)" (Cited in the European Search Report), retrieved from the World-Wide-Web at brenntag.com/media/documents/bsi/product_data_sheets/life_science/sumitomo/aqupec_ser_w_150c_pds.pdf.
Extended European Search Report issued for Counterpart European Patent Application No. 17774738.3 (dated Sep. 5, 2019).
Office Action issued for the counterpart Japanese Patent Appln. No. JP 2018-509225 (dated Mar. 2, 2021).

* cited by examiner

*Primary Examiner* — Matthew P Coughlin
*Assistant Examiner* — Thurman Wheeler
(74) *Attorney, Agent, or Firm* — Knobbe, Martens, Olson & Bear, LLP

(57) ABSTRACT

There is provided a gel composition that can be suitably used as a thickener for cosmetic preparations and the like. A gel composition comprising a neutralized product of an alkyl-modified carboxyl group-containing polymer, which is a copolymer of monomers comprising 100 parts by mass of (meth)acrylic acid (a), 2.5 to 5 parts by mass of a (meth)acrylic acid alkyl ester (b) in which the alkyl group has 18 to 24 carbon atoms, and 0.1 part by mass or less of a compound (c) having two or more ethylenically unsaturated groups; and at least one of an anionic emulsifier and a nonionic emulsifier.

10 Claims, No Drawings

GEL COMPOSITION, COSMETIC, AND METHOD FOR PRODUCING GEL COMPOSITION

TECHNICAL FIELD

The present invention relates to a gel composition that can be suitably used as a thickener for cosmetic preparations in the form of viscous solutions or gels used for, for example, hair care products such as shampoos or skin care products such as body washes and facial cleansers, a method for producing the gel composition, and a cosmetic preparation comprising the gel composition.

BACKGROUND ART

As thickeners for cosmetic preparations, for example, natural materials such as xanthan gum, semi-synthetic materials such as hydroxyethyl cellulose, and synthetic materials such as carboxyvinyl polymers and alkyl-modified carboxyvinyl polymers have been extensively used. In particular, carboxyl group-containing polymers such as carboxyvinyl polymers and alkyl-modified carboxyvinyl polymers are used for various cosmetic preparations, because they exhibit excellent thickening properties even when used in small amounts, and can control the after-feel of the cosmetic preparation.

Those known as such carboxyl group-containing polymers include alkyl-modified carboxyvinyl polymers such as, for example, a carboxyvinyl polymer obtained by reacting acrylic acid and a pentaerythritol allyl ether as a crosslinking agent in a specific solvent mixture (see Patent Literature 1), a copolymer obtained by reacting a specific amount of an olefinic unsaturated carboxylic acid monomer and a specific amount of a (meth)acrylic acid alkyl ester (in which the alkyl group has 10 to 30 carbon atoms) (see Patent Literature 2), a copolymer obtained by reacting a specific amount of an olefinic unsaturated carboxylic acid monomer, a specific amount of a (meth)acrylic acid alkyl ester (in which the alkyl group has 10 to 30 carbon atoms), and a crosslinking agent (see Patent Literature 3), and a copolymer obtained by reacting an olefinic unsaturated carboxylic acid monomer and a (meth)acrylic acid alkyl ester (in which the alkyl group has 8 to 30 carbon atoms) (see Patent Literature 4). Typically, these carboxyl group-containing polymers are dissolved in water or the like and then neutralized with an alkaline component to give about 0.1 to 1% by mass neutral viscous solutions, which are used for cosmetic preparations.

These neutral viscous solutions are disadvantageous in that the viscosity or stability decreases, or a portion of the polymer precipitates, under the influence of an emulsifier that is a main ingredient of cosmetic preparations.

CITATION LIST

Patent Literature

Patent Literature 1: U.S. Pat. No. 5,342,911
Patent Literature 2: JP 51-6190 A
Patent Literature 3: JP 59-232107 A
Patent Literature 4: Specification of U.S. Pat. No. 5,004,598

SUMMARY OF INVENTION

Technical Problem

It is a main object of the present invention to provide a gel composition that can be suitably used as a thickener for cosmetic preparations and the like, a method for producing the gel composition, and a cosmetic preparation comprising the gel composition.

Solution to Problem

The inventors of the present invention conducted extensive research to solve the aforementioned problem. As a result, they found that in a gel composition comprising a neutralized product of an alkyl-modified carboxyl group-containing polymer, which is a copolymer of monomers comprising 100 parts by mass of (meth)acrylic acid (a), 2.5 to 5 parts by mass of a (meth)acrylic acid alkyl ester (b) in which the alkyl group has 18 to 24 carbon atoms, and 0.1 part by mass or less of a compound (c) having two or more ethylenically unsaturated groups, and at least one of an anionic emulsifier and a nonionic emulsifier, the difference in viscosity before and after mixing of at least one of the anionic emulsifier and the nonionic emulsifier is very large. On the basis of this, they found that a gel composition having a suitably high viscosity can be obtained by dispersing or dissolving desired components highly homogeneously at a low viscosity before mixing of the anionic emulsifier or the nonionic emulsifier, and then adding at least one of the anionic emulsifier or the nonionic emulsifier. This gel composition exhibits excellent thickening properties, and can be suitably used as a thickener for cosmetic preparations and the like.

In summary, the present invention provides aspects of the invention comprising the following features:

Item 1. A gel composition comprising:
a neutralized product of an alkyl-modified carboxyl group-containing polymer, which is a copolymer of monomers comprising 100 parts by mass of (meth)acrylic acid (a), 2.5 to 5 parts by mass of a (meth)acrylic acid alkyl ester (b) in which the alkyl group has 18 to 24 carbon atoms, and 0.1 part by mass or less of a compound (c) having two or more ethylenically unsaturated groups; and
at least one of an anionic emulsifier and a nonionic emulsifier.

Item 2. The gel composition according to item 1, wherein the content of the anionic emulsifier is 0.05 to 1% by mass (solids content), and the pH of the composition is 4 to 5.6.

Item 3. The gel composition according to item 1, wherein the content of the nonionic emulsifier is 0.05 to 1% by mass (solids content), and the pH of the composition is 4 to 13.

Item 4. The gel composition according to any one of items 1 to 3, wherein the compound (c) having two or more ethylenically unsaturated groups is at least one selected from the group consisting of pentaerythritol allyl ethers, diethylene glycol diallyl ether, polyethylene glycol diallyl ether, and polyallylsaccharose.

Item 5. The gel composition according to any one of items 1 to 4, wherein the anionic emulsifier is an alkyl sulfate, and the nonionic emulsifier is a polyoxyethylene alkyl ether.

Item 6. A cosmetic preparation comprising the gel composition according to any one of items 1 to 5.

Item 7. A method for producing a gel composition comprising the steps of:
mixing an alkyl-modified carboxyl group-containing polymer, which is a copolymer of monomers comprising 100 parts by mass of (meth)acrylic acid (a), 2.5 to 5 parts by mass of a (meth)acrylic acid alkyl ester (b) in which the alkyl group has 18 to 24 carbon atoms, and 0.1 part by mass or less of a compound (c) having two or more ethylenically unsaturated groups, with an alkaline component, to prepare a neutralized product of the alkyl-modified carboxyl group-containing polymer; and mixing the neutralized product of the alkyl-modified carboxyl group-containing polymer with at least one of an anionic emulsifier and a nonionic emulsifier.

Advantageous Effects of Invention

The present invention can provide a gel composition that can be suitably used as a thickener for cosmetic preparations and the like, and a method for producing the gel composition.

DESCRIPTION OF EMBODIMENTS

A gel composition according to the present invention comprises a neutralized product of an alkyl-modified carboxyl group-containing polymer, which is a copolymer of monomers comprising 100 parts by mass of (meth)acrylic acid (a), 2.5 to 5 parts by mass of a (meth)acrylic acid alkyl ester (b) in which the alkyl group has 18 to 24 carbon atoms, and 0.1 part by mass or less of a compound (c) having two or more ethylenically unsaturated groups; and at least one of an anionic emulsifier and a nonionic emulsifier. The gel composition of the present invention, a method for producing the gel composition, and a cosmetic preparation comprising the gel composition will be hereinafter described in detail.

As used herein, the term "(meth)acrylic acid" collectively refers to "acrylic acid and methacrylic acid". As used herein, the term "neutral viscous solution" refers to a viscous liquid obtained by mixing an aqueous dispersion of an alkyl-modified carboxyl group-containing polymer with an alkaline component (for example, an alkali metal hydroxide such as sodium hydroxide, or an amine such as triethanolamine or diisopropanolamine) such that the pH of the aqueous dispersion of the alkyl-modified carboxyl group-containing polymer is adjusted to a predetermined value (typically a pH of about 3.5 to 6.5). The term "1% by mass neutral viscous solution" refers to a neutral viscous solution containing 1% by mass of a neutralized product of the alkyl-modified carboxyl group-containing polymer.

In the present invention, the neutralized product of the alkyl-modified carboxyl group-containing polymer is a compound obtained by partially or completely neutralizing the alkyl-modified carboxyl group-containing polymer with the above-mentioned alkaline component. In the gel composition of the present invention (in particular, with a pH of about 3.5 to 6.5), the neutralized product of the alkyl-modified carboxyl group-containing polymer is typically a partially neutralized product of the alkyl-modified carboxyl group-containing polymer. Before neutralization, the alkyl-modified carboxyl group-containing polymer typically has a pH of about 2.5 to 3.

The alkyl-modified carboxyl group-containing polymer is a copolymer of 100 parts by mass of (meth)acrylic acid (hereinafter sometimes referred to as the component (a)), 2.5 to 5 parts by mass of a (meth)acrylic acid alkyl ester in which the alkyl group has 18 to 24 carbon atoms (hereinafter sometimes referred to as the component (b)), and 0.1 part by mass or less of a compound having two or more ethylenically unsaturated groups (hereinafter sometimes referred to as the component (c)). Specifically, the alkyl-modified carboxyl group-containing polymer of the present invention is a copolymer of at least the components (a) and (b), as well as optionally the component (c).

In the present invention, at least one of acrylic acid and methacrylic acid can be used as (meth)acrylic acid (the component (a)).

The (meth)acrylic acid alkyl ester in which the alkyl group has 18 to 24 carbon atoms (the component (b)) is an ester of (meth)acrylic acid and a higher alcohol in which the alkyl group has 18 to 24 carbon atoms. Specific examples of the component (b) include an ester of (meth)acrylic acid and stearyl alcohol (i.e., stearyl (meth)acrylate), an ester of (meth)acrylic acid and eicosanol (i.e., eicosanyl (meth)acrylate), an ester of (meth)acrylic acid and behenyl alcohol (i.e., behenyl (meth)acrylate), and an ester of (meth)acrylic acid and tetracosanol (i.e., tetracosanyl (meth)acrylate). Among the above, stearyl methacrylate, eicosanyl methacrylate, behenyl methacrylate, and tetracosanyl methacrylate, for example, can be suitably used, because they can achieve an excellent thickening effect obtained by a gel composition having high transparency, even in the presence of the neutralized product of the alkyl-modified carboxyl group-containing polymer and a cationic polymer that is often blended into a cosmetic preparation or the like.

In the alkyl-modified carboxyl group-containing polymer, the monomer-constituting components (b) may be used alone or in combinations of two or more. When two or more components (b) are used for copolymerization, trade name BLEMMER VMA70 from NOF Corporation (a mixture of 10 to 20 parts by mass of stearyl methacrylate, 10 to 20 parts by mass of eicosanyl methacrylate, 59 to 80 parts by mass of behenyl methacrylate, and 1 part by mass or less of tetracosanyl methacrylate), for example, can be used.

The proportion of the component (b) in the alkyl-modified carboxyl group-containing polymer is 2.5 to 5 parts by mass per 100 parts by mass of (meth)acrylic acid (the component (a)). In order to effectively increase the viscosity of the gel composition in the presence of at least one of the anionic emulsifier and the nonionic emulsifier, the proportion of the component (b) is, for example, preferably 1 to 3 parts by mass per 100 parts by mass of the component (a). If the proportion of the component (b) is less than 2.5 parts by mass per 100 parts by mass of the component (a), the viscosity of the gel composition tends to decrease in the presence of at least one of the anionic emulsifier and the nonionic emulsifier, whereas if the proportion is more than 5 parts by mass, the viscosity of the gel composition also tends to decrease.

The compound having two or more ethylenically unsaturated groups (the component (c)) is a compound having two or more polymerizable ethylenically unsaturated groups. In the present invention, the component (c) optionally constitutes a monomer of the alkyl-modified carboxyl group-containing polymer. Preferred specific examples of the component (c) include polyallyl ethers of pentaerythritol such as pentaerythritol diallyl ether, pentaerythritol triallyl ether, and pentaerythritol tetraallyl ether (each of them and mixtures of two or more of them are collectively referred to as "pentaerythritol allyl ethers"), diethylene glycol diallyl ether, polyethylene glycol diallyl ether, and polyallylsaccharose. In the alkyl-modified carboxyl group-containing polymer, the optional monomer-constituting components (c) may be used alone or in combinations of two or more.

The proportion of the component (c) in the alkyl-modified carboxyl group-containing polymer is, for example, 0.1 part by mass or less, preferably 0.0001 to 0.05 part by mass, and more preferably 0.001 to 0.044 part by mass, per 100 parts by mass of (meth)acrylic acid (the component (a)). If the proportion of the component (c) is more than 0.1 part by mass, the viscosity of the gel composition tends to decrease, and the stability of the cosmetic preparation obtained using the gel composition may deteriorate.

The alkyl-modified carboxyl group-containing polymer of the present invention may be copolymerized with a monomer other than the components (a) to (c) (another monomer copolymerizable with at least one of the components (a) to (c)). For example, lauryl (meth)acrylate may be used in a proportion of more than 0 part by mass and 1 part by mass or less, per total 100 parts by mass of the components (a) to (c). In the present invention, although the total proportion of the components (a) to (c) in the monomers constituting the alkyl-modified carboxyl group-containing polymer is not particularly limited, it is, for example, preferably 50% by mass or more, more preferably about 80 to 100% by mass, still more preferably about 90 to 100% by mass, and particularly preferably about 95 to 100% by mass. The total proportion may be substantially 100% by mass.

The method for producing the alkyl-modified carboxyl group-containing polymer is not particularly limited, and examples include a method in which raw materials including at least the components (a) and (b), as well as a polymerization initiator, are added to a solvent to form a solution, and the solution is heated with stirring in an inert gas atmosphere to carry out the polymerization.

Examples of inert gases for creating the inert gas atmosphere include, but are not particularly limited to, nitrogen gas and argon gas.

The solvent is not particularly limited as long as it dissolves at least the components (a) and (b), but does not dissolve the alkyl-modified carboxyl group-containing polymer produced, and does not inhibit the copolymerization reaction. Specific examples of the solvent include hydrocarbon solvents such as normal pentane, normal hexane, normal heptane, cyclopentane, and cyclohexane; and ester-based solvents such as methyl acetate, ethyl acetate, propyl acetate, and butyl acetate. These solvents may be used alone or in combinations of two or more. Among these solvents, normal hexane, normal heptane, and ethyl acetate, for example, are suitably used.

The amount of the solvent to be used is preferably 300 to 5,000 parts by mass per 100 parts by mass of the component (a), in order to improve the ease of stirring, and from an economic viewpoint.

The polymerization initiator is preferably a radical polymerization initiator, for example. Specific examples of the polymerization initiator include α,α'-azoisobutyronitrile, 2,2'-azobis(2,4-dimethylvaleronitrile), and 2,2'-azobis(methylisobutyrate). Among the above, 2,2'-azobis(methylisobutyrate) is preferred in order to obtain an alkyl-modified carboxyl group-containing polymer having a high molecular weight. These polymerization initiators may be used alone or in combinations of two or more.

The amount of the polymerization initiator to be used is preferably about 0.00003 to 0.002 mol per mole of the component (a), in order to keep an appropriate reaction rate. When the amount of the polymerization initiator used is 0.00003 mol or more, the reaction rate is not excessively slow, which is economical. Moreover, when the amount of the polymerization initiator used is 0.002 mol or less, abrupt progress of the polymerization is suppressed, and the polymerization reaction is easy to control.

The polymerization temperature is preferably about 50 to 90° C., and more preferably about 55 to 75° C., in order to keep an appropriate reaction rate.

The polymerization time is typically about 0.5 to 5 hours, although it may vary depending on the polymerization temperature and the like.

The alkyl-modified carboxy group-containing polymer can be obtained by removing the solvent from the dispersion after the polymerization, by heating to 80 to 130° C., for example, in order to reduce the drying time to suppress agglomeration of the copolymer. When the heating temperature at this time is 80° C. or more, the drying time can be reduced. Moreover, when the heating temperature is 130° C. or less, a decrease in the dispersibility of the alkyl-modified carboxyl group-containing polymer in water can be suitably suppressed.

In order to increase the viscosity and transparency of the gel composition even in the presence of at least one of the anionic emulsifier and the nonionic emulsifier, and increase the difference in viscosity before and after mixing of at least one of the anionic emulsifier and the nonionic emulsifier, the alkyl-modified carboxyl group-containing polymer (in the absence of at least one of the anionic emulsifier and the nonionic emulsifier) preferably has a viscosity at 25° C. of 5,000 mPa·s or less, more preferably about 100 to 1000 mPa·s, when in the form of a 1% by mass neutral viscous solution.

In the present invention, the term "viscosity" refers to a value measured using the method described in the Examples.

In the gel composition of the present invention, although the content of the neutralized product of the alkyl-modified carboxyl group-containing polymer is not particularly limited, it is preferably about 0.1 to 2% by mass, and more preferably about 0.5 to 1.5% by mass.

Preferred examples of the anionic emulsifier include the following, in order to increase the viscosity of the gel composition in the presence of the above-described neutralized product of the alkyl-modified carboxyl group-containing polymer: polyoxyethylene alkyl ether sulfates such as sodium polyoxyethylene (hereinafter sometimes abbreviated as POE) lauryl ether sulfate and ammonium POE isodecyl ether sulfate; polyoxyethylene alkyl ether phosphates such as POE lauryl ether phosphate and POE tridecyl ether phosphate; alkyl sulfates such as ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, sodium lauryl sulfate, sodium laureth sulfate, potassium laureth sulfate, and potassium lauryl sulfate; sulfonates such as sodium dodecylbenzenesulfonate; sulfosuccinates such as sodium dioctyl sulfosuccinate; and fatty acid salts such as potassium laurate and sodium stearate. Among the above, lauryl sulfates such as sodium lauryl sulfate and laureth sulfates such as sodium laureth sulfate are preferably used, because they can achieve high foaming when the gel composition of the present invention is blended into a cosmetic preparation, and can achieve a conditioning effect. These anionic emulsifiers may be used alone or in combinations of two or more.

Preferred examples of the nonionic emulsifier include the following, in order to increase the viscosity of the gel composition in the presence of the above-described neutralized product of the alkyl-modified carboxyl group-containing polymer: polyoxyethylene alkyl ethers such as polyoxyethylene lauryl ether, POE tridecyl ether, POE cetyl ether, and POE stearyl ether; polyoxyethylene polyoxypropylene alkyl ethers such as polyoxyethylene polyoxypropylene (hereinafter sometimes abbreviated as POP) lauryl ether, POE POP cetyl ether, and POE POP stearyl ether; polyoxyethylene sorbitan fatty acid esters such as POE sorbitan monooleate, POE sorbitan monostearate, and POE sorbitan distearate; polyoxyethylene sorbitol fatty acid esters such as POE sorbitol monooleate, POE sorbitol monostearate, and POE sorbitol distearate; polyoxyethylene glycerin fatty acid esters such as POE glycerin monooleate, POE glycerin monostearate, and POE glycerin distearate; polyoxyethylene fatty acid esters such as POE monooleate, POE monostearate, and POE distearate; polyoxyethylene castor oil derivatives such as POE castor oil, POE hydrogenated castor oil, POE hydrogenated castor oil monolaurate, and POE hydrogenated castor oil monoisostearate; polyoxyethylene alkylamines such as POE laurylamine and POE stearylamine; sucrose fatty acid esters such as sucrose laurate and sucrose myristate. Among the above, polyoxyethylene lauryl ether, for example, is preferably used because it can achieve high foaming when the gel composition of the present invention is blended into a cosmetic preparation, is mildly irritating, and can achieve a conditioning effect. These nonionic emulsifiers may be used alone or in combinations of two or more.

Furthermore, in the present invention, the anionic emulsifier and the nonionic emulsifier may be used in combination.

With regard to the contents of the anionic emulsifier and the nonionic emulsifier in the gel composition of the present invention, for example, in order to allow the gel composition of the present invention to exhibit high viscosity characteristics even when the pH of the composition is set to a low value (for example, a pH in the range of about 4 to 5.6), the content of the anionic emulsifier is preferably about 0.05 to 1% by mass (solids content), and more preferably about 0.1 to 0.5% by mass (solids content). Furthermore, in order to allow the gel composition of the present invention to exhibit high viscosity characteristics even when the pH of the composition is set in a wide range of values (for example, a pH in the range of about 4 to 13), the content of the nonionic emulsifier is preferably about 0.05 to 1% by mass (solids content), and more preferably about 0.1 to 0.5% by mass (solids content).

In the gel composition of the present invention, for example, when the amount of the anionic emulsifier is set to about 0.05 to 1% by mass (solids content), and more preferably about 0.1 to 0.5% by mass (solids content), a gel composition having a high viscosity at a low pH in the range of 4 to 5.6 can be obtained, and the gel composition can be suitably used as a thickener for cosmetic preparations and the like. Furthermore, in the gel composition of the present invention, the difference in viscosity before and after addition of the anionic emulsifier is particularly large in this low pH range. Thus, a gel composition having a suitably high viscosity in the low pH range can be obtained by, for example, mixing various components homogeneously at a low viscosity before addition of the anionic emulsifier, and then adding the anionic emulsifier.

Moreover, in the gel composition of the present invention, for example, when the amount of the nonionic emulsifier is set to about 0.05 to 1% by mass (solids content), and more preferably about 0.1 to 0.5% by mass (solids content), a gel composition having a high viscosity under a wide pH range of 4 to 13 can be obtained, and the gel composition can be suitably used as a thickener for cosmetic preparations and the like. Furthermore, in the gel composition of the present invention, the difference in viscosity before and after addition of the nonionic emulsifier is particularly large in this wide pH range. Thus, a gel composition having a suitably high viscosity in the low pH range can be obtained by, for example, mixing various components homogeneously at a low viscosity before addition of the nonionic emulsifier, and then adding the nonionic emulsifier.

In the gel composition of the present invention, when the pH is low, i.e., from 4 to 5.6, a viscosity of, for example, 15,000 mPa·s or more, and even 20,000 mPa·s or more can be achieved by setting the content of the anionic emulsifier to about 0.05 to 1% by mass (solids content). In this case, the upper limit of the viscosity is typically about 200,000 mPa·s.

Furthermore, in the gel composition of the present invention, when the pH is in a wide range of 4 to 13, a viscosity of, for example, 20,000 mPa·s or more, and even 30,000 mPa·s or more can be achieved by setting the content of the nonionic emulsifier to about 0.05 to 1% by mass (solids content). In this case, the upper limit of the viscosity is typically about 200,000 mPa·s.

Although a detailed mechanism by which the gel composition of the present invention has a high viscosity and can be suitably used as a thickener for cosmetic preparations and the like is not necessarily clear, it can be assumed to be as follows, for example: In the present invention, because the neutralized product of the alkyl-modified carboxyl group-containing polymer contained in the gel composition is obtained by copolymerizing the components (a) to (c) in the above-described predetermined amounts, the neutralized product of the alkyl-modified carboxyl group-containing polymer and at least one of the anionic emulsifier and the nonionic emulsifier suitably form aggregates in water with an increased thickness, thus forming a gel composition having a high viscosity.

The gel composition of the present invention typically contains water in addition to the components (a) to (c). Although the content of water in the gel composition of the present invention is not particularly limited, it is preferably 91.4 to 99.3% by mass, and more preferably 92.0 to 99.0% by mass.

The gel composition of the present invention may also contain various additives, such as other thickeners, alcohols, pH adjusters, moisturizers, oils, salts, cationic surfactants, amphoteric surfactants, chelating agents, preservatives, antioxidants, ultraviolet absorbers, colorants, and perfumes, as long as they do not impair the purpose of the composition. The gel composition of the present invention can be suitably used as a thickener for cosmetic preparations in the form of viscous solutions or gels used for, for example, hair care products such as shampoos or skin care products such as body washes and facial cleansers. The cosmetic preparation of the present invention contains the gel composition of the present invention, and may further contain various cosmetic ingredients to be blended into cosmetic preparations.

Although the method for producing the gel composition of the present invention is not particularly limited, the gel composition can be suitably produced using, for example, a method including the following steps:

mixing the alkyl-modified carboxyl group-containing polymer, which is a copolymer of monomers comprising 100 parts by mass of (meth)acrylic acid (a), 2.5 to 5 parts by mass of a (meth)acrylic acid alkyl ester (b) in which the alkyl group has 18 to 24 carbon atoms, and 0.1 part by mass or less of a compound (c) having two or more ethylenically unsaturated groups, with the alkaline component, to prepare a neutralized product of the alkyl-modified carboxyl group-containing polymer; and mixing the neutralized product of the alkyl-modified carboxyl group-containing polymer with at least one of the anionic emulsifier and the nonionic emulsifier.

In the above-described method, the pH of the gel composition can be adjusted to a desired value by adding the alkaline component at least either before or after mixing of at least one of the anionic emulsifier and the nonionic emulsifier.

The method for producing the gel composition of the present invention may further include mixing various additives. Mixing of the various additives can be performed either before or after mixing of the neutralized product of the alkyl-modified carboxyl group-containing polymer and at least one of the anionic emulsifier and the nonionic emulsifier.

EXAMPLES

The present invention will be hereinafter described in detail by way of examples and comparative examples, although the present invention is not limited to the examples.

(Viscosity Measurement)

Using a BH-type rotational viscometer, the rotational speed of a spindle rotor No. 7 was set to 20 rotations per minute at 25° C., and the viscosity after 1 minute was measured.

Production Example 1

A 500-mL four-necked flask equipped with a stirrer, a thermometer, a nitrogen inlet tube, and a condenser tube was charged with 45 g (0.625 mol) of acrylic acid, 1.4 g of BLEMMER VMA70 (NOF Corporation; a mixture containing 10 to 20 parts by mass of stearyl methacrylate, 10 to 20 parts by mass of eicosanyl methacrylate, 59 to 80 parts by mass of behenyl methacrylate, and 1 part by mass or less of tetracosanyl methacrylate), 0.02 g of a pentaerythritol allyl ether (a mixture of pentaerythritol triallyl ether and pentaerythritol tetraallyl ether), 150 g of normal hexane, and 0.081 g (0.00035 mol) of 2,2'-azobismethylisobutyrate. Then, while the contents of the flask were being homogeneously stirred, nitrogen gas was blown into the solution to remove oxygen in the flask. Then, while stirring and blowing of nitrogen gas were being continued, the flask was placed in an oil bath set at 60 to 65° C. to heat the contents, and kept at the temperature for 4 hours. Then, the temperature of the oil bath was set to 90° C. to remove the normal hexane. Then, the contents of the flask were transferred into a vacuum dryer (Vacuum Drying Oven DP33 from Yamato Scientific Co., Ltd.), the temperature of the oven was set to 110° C. and the pressure of the oven was set to 10 mmHg, and the contents were dried for 8 hours to obtain 45 g of an alkyl-modified carboxyl group-containing polymer (polymer 1) as a white powder.

Production Example 2

Following the procedure of Production Example 1, except for changing the amount of BLEMMER VMA70 (NOF Corporation) used to 1.125 g, and changing the amount of the pentaerythritol allyl ether (a mixture of pentaerythritol triallyl ether and pentaerythritol tetraallyl ether) used to 0.135 g from 0.02 g, 45 g of an alkyl-modified carboxyl group-containing polymer (polymer 2) was obtained as a white powder.

<Evaluation of Relationships Between pH and Viscosity of Gel Compositions>

Referential Example 1

Using an ultrahigh-speed stirring system T. K. ROBO-MIX (Primix Corporation) equipped with a Disper blade (diameter: 40 mm), 10 g of the polymer 1 was gradually added into a 2-L beaker containing 987.7 g of distilled water and dispersed at a stirring rate of 5000 rotations per minute. After stirring was performed for 10 minutes at 5000 rotations per minute, the stirring rate was reduced to 3000 rotations per minute, and stirring was continued for 20 minutes. Then, at a stirring rate of 1400 rotations per minute, 2.3 g of an 18% by mass aqueous solution of sodium hydroxide was added, and the contents were homogenously stirred to prepare a neutral viscous solution having a pH of about 3.8. Next, the pH of the neutral viscous solution was changed as shown in Table 1, by adding predetermined amounts of an 18% by mass aqueous solution of sodium hydroxide, and homogenously stirring the mixtures. Then, the viscosities at various pHs of the neutral viscous solution were measured (the emulsifier content: 0% by mass in Table 1). The results are shown in Table 1.

TABLE 1

| Referential Example 1 Polymer 1/Emulsifier Content: 0% by mass | |
|---|---|
| pH | Viscosity [mPa · s] |
| 3.81 | 100 |
| 4.01 | 172 |
| 4.23 | 372 |
| 4.42 | 910 |
| 4.62 | 1,850 |
| 4.84 | 3,500 |
| 5.00 | 4,600 |
| 5.20 | 4,920 |
| 5.31 | 5,020 |
| 5.64 | 1,540 |
| 5.77 | 960 |
| 5.95 | 450 |
| 6.26 | 272 |
| 6.39 | 250 |
| 6.58 | 220 |
| 6.75 | 180 |
| 7.12 | 120 |
| 12.96 | 100 |

Examples 1 to 4

A neutral viscous solution in which the polymer 1 was adjusted to a pH of about 3.8 as in Referential Example 1 was divided into 144-g portions in 200-L beakers. Then, using four paddle blades (diameter: 50 mm) at a stirring rate of 500 rotations per minute, sodium lauryl sulfate (Emal 10 G from Kao Corporation, 98% by mass sodium lauryl sulfate) and distilled water or sodium laureth sulfate (Emal 20 C from Kao Corporation, 25% by mass sodium laureth sulfate) and distilled water (in an amount to give 150 g of a gel composition for each case) were slowly added such that each of the contents shown in Table 2 (the sodium lauryl sulfate content or the sodium laureth sulfate content was 0.1% by mass (solids content) or 0.50% by mass (solids content) for each case) was achieved. Then, the stirring rate was increased to 1000 rotations per minute, and mixing was performed for 1 hour to prepare each gel composition. Next, the pH of the gel composition was changed as shown in Table 2, by adding predetermined amounts of an 18% by mass aqueous solution of sodium hydroxide to the gel composition obtained, and homogenously stirring the mixtures. Then, the viscosities at various pHs of the neutral viscous solution were measured. The results are shown in Table 2.

TABLE 2

| Example 1 Polymer 1/Sodium Lauryl Sulfate Content (Solids Content) 0.1% by mass | | Example 2 Polymer 1/Sodium Lauryl Sulfate Content (Solids Content) 0.5% by mass | | Example 3 Polymer 1/Sodium Laureth Sulfate Content (Solids Content) 0.1% by mass | | Example 4 Polymer 1/Sodium Laureth Sulfate Content (Solids Content) 0.5% by mass | |
|---|---|---|---|---|---|---|---|
| pH | Viscosity [mPa · s] | pH | Viscosity [mPa · s] | pH | Viscosity [mPa · s] | pH | Viscosity [mPa · s] |
| 4.31 | 18,000 | 4.28 | 29,600 | 4.35 | 15,200 | 4.04 | 14,500 |
| 4.53 | 28,400 | 4.65 | 45,600 | 4.81 | 14,200 | 4.18 | 32,000 |
| 4.99 | 25,600 | 4.91 | 56,000 | | | 4.34 | 49,000 |
| 5.22 | 22,400 | 5.23 | 30,000 | | | 4.44 | 57,000 |
| 5.5 | 19,600 | 5.57 | 14,600 | | | 4.7 | 30,000 |

As is evident from the results shown in Table 2, it is found that in Examples 1 to 4, gel compositions having high viscosities are obtained at low pHs in the range of about 4 to 5.6. It is also found that because the difference in viscosity before and after addition of the anionic emulsifier is very large, a gel composition having a suitably high viscosity in the low pH range can be obtained by mixing the various components homogeneously at a low viscosity before addition of the anionic emulsifier, and then adding the anionic emulsifier. That is, it is found that, in the low pH range, before addition of the anionic emulsifier (the emulsifier content: 0% by mass (Referential Example 1) in Table 1), the viscosity of each composition is very low, and the components can be readily homogeneously dispersed or dissolved; subsequently, a predetermined amount of the anionic emulsifier is added (the sodium lauryl sulfate content or the sodium laureth sulfate content is 0.1 or 0.50% by mass for each case), and thereby a gel composition having a high viscosity can be obtained.

Referential Example 2

Following the procedure of Referential Example 1, except for using the polymer 2 instead of the polymer 1, a neutral viscous solution having a pH of about 3.8 was prepared. Next, the pH of the neutral viscous solution was changed as shown in Table 3, by adding predetermined amounts of an 18% by mass aqueous solution of sodium hydroxide, and homogeneously stirring the mixtures. Then, the viscosities at various pHs of the neutral viscous solution were measured (the emulsifier content: 0% by mass in Table 3). The results are shown in Table 3.

TABLE 3

Referential Example 2
Polymer 2/Emulsifier Content: 0% by mass

| pH | Viscosity [mPa · s] |
|---|---|
| 3.99 | 25,800 |
| 4.56 | 27,800 |
| 5.15 | 27,800 |
| 5.7 | 26,900 |
| 6.45 | 25,900 |
| 6.82 | 25,600 |
| 7.61 | 25,100 |
| 10.34 | 24,500 |

Comparative Example 1

A neutral viscous solution in which the polymer (a polymer having a high crosslinking degree, as compared to the polymer 1) was adjusted to a pH of about 3.8 as in Referential Example 2 was divided into 144-g portions in 200-L beakers. Then, using four paddle blades (diameter: 50 mm) at a stirring rate of 500 rotations per minute, sodium lauryl sulfate (Emal 10 G from Kao Corporation, 98% by mass sodium lauryl sulfate) and distilled water (in an amount of 5.85 g to give 150 g of a gel composition) were slowly added such that the content shown in Table 4 (the sodium lauryl sulfate content was 0.1% by mass (solids content)) was achieved. Then, the stirring rate was increased to 1000 rotations per minute, and mixing was performed for 1 hour to prepare a gel composition. Next, the pH of the gel composition was changed as shown in Table 4, by adding predetermined amounts of an 18% by mass aqueous solution of sodium hydroxide to the gel composition obtained, and homogeneously stirring the mixtures. Then, the viscosities at various pHs of the neutral viscous solution were measured. The results are shown in Table 4.

TABLE 4

Comparative Example 1
Polymer 2/Sodium Lauryl Sulfate Content: 0.1% by mass

| pH | Viscosity [mPa · s] |
|---|---|
| 4.35 | 23,500 |
| 4.8 | 38,200 |
| 5.26 | 43,500 |
| 5.91 | 33,200 |

As is evident from the results shown in Tables 3 and 4, it is found that when the polymer 2 (a polymer having a high crosslinking degree, as compared to the polymer 1) is used as in Referential Example 2, because the viscosity before addition of the anionic emulsifier (the emulsifier content: 0% by mass (Referential Example 2) in Table 3) is high in the low pH range from 4 to 5.6, the components are less readily homogenously dispersed or dissolved than in Examples 1 to 4. It is found that even in Comparative Example 1 in which the anionic emulsifier is further added to the polymer 2 of Referential Example 2, the viscosity of the gel composition does not significantly increase.

Examples 5 and 6

A neutral viscous solution in which the polymer 1 was adjusted to a pH of about 3.8 as in Referential Example 1 was divided into 144-g portions in 200-L beakers. Then, using four paddle blades (diameter: 50 mm) at a stirring rate of 500 rotations per minute, polyoxyethylene lauryl ether (EMULGEN 108 from Kao Corporation, 100% by mass polyoxyethylene lauryl ether) and distilled water (in an amount to give 150 g of a gel composition for each case) were slowly added such that each of the contents shown in Table 5 (the polyoxyethylene lauryl ether content was 0.1% by mass (solids content) or 0.50% by mass (solids content) for each case) was achieved. Then, the stirring rate was increased to 1000 rotations per minute, and mixing was performed for 1 hour to prepare each gel composition. Next, the pH of the gel composition was changed as shown in Table 5, by adding predetermined amounts of an 18% by mass aqueous solution of sodium hydroxide to the gel composition obtained, and homogeneously stirring the mixtures. Then, the viscosities at various pHs of the neutral viscous solution were measured. The results are shown in Table 5.

TABLE 5

| Example 5 Polymer 1/ Polyoxyethylene Lauryl Ether Content: 0.1% by mass | | Example 6 Polymer 1/ Polyoxyethylene Lauryl Ether Content: 0.5% by mass | |
|---|---|---|---|
| pH | Viscosity [mPa · s] | pH | Viscosity [mPa · s] |
| 4.21 | 25,600 | 3.92 | 46,600 |
| 4.4 | 31,400 | 4.3 | 54,000 |
| 4.63 | 33,400 | 4.61 | 80,000 |
| 4.93 | 33,200 | 4.91 | 115,000 |
| 5.14 | 32,200 | 5.42 | 117,000 |
| 5.35 | 32,000 | 6 | 39,800 |
| 5.74 | 31,200 | 6.47 | 14,800 |
| 6.02 | 29,000 | 7.11 | 7,000 |
| 6.39 | 28,400 | 11.81 | 4,600 |
| 6.68 | 24,400 | | |
| 7.05 | 17,600 | | |
| 7.37 | 13,800 | | |
| 8.01 | 11,600 | | |
| 8.47 | 11,000 | | |
| 11.99 | 11,400 | | |

As is evident from the results shown in Table 5, it is found that in Examples 5 and 6, gel compositions having high viscosities can be obtained in a wide pH range of about 4 to 13, It is also found that because the difference in viscosity before and after addition of the nonionic emulsifier is very large, a gel composition having a suitably high viscosity in the wide pH range can be obtained by mixing the various components homogeneously at a low viscosity before addition of the nonionic emulsifier, and then adding the nonionic emulsifier. That is, it is found that, in the wide pH range, before addition of the nonionic emulsifier (the emulsifier content: 0% by mass (Referential Example 1) in Table 1), the viscosity of each composition is very low, and the components can be readily homogeneously dispersed or dissolved; subsequently, a predetermined amount of the nonionic emulsifier is added (the polyoxyethylene lauryl ether content is 0.1% by mass (solids content) or 0.50% by mass (solids content) for each case), and thereby a gel composition having a high viscosity can be obtained.

Comparative Example 2

A neutral viscous solution in which the polymer 2 (a polymer having a high crosslinking degree, as compared to the polymer 1) was adjusted to a pH of about 3.8 as in Referential Example 2 was divided into 144-g portions in 200-L beakers. Then, using four paddle blades (diameter: 50 mm) at a stirring rate of 500 rotations per minute, polyoxyethylene lauryl ether (EMULGEN 108 from Kao Corporation, 100% by mass polyoxyethylene lauryl ether) and distilled water (in an amount of 5.25 g to give 150 g of a gel composition) were slowly added such that the content shown in Table 6 (the polyoxyethylene lauryl ether content was 0.50% by mass (solids content)) was achieved. Then, the stirring rate was increased to 1000 rotations per minute, and mixing was performed for 1 hour to prepare a gel composition. Next, the pH of the gel composition was changed as shown in Table 6, by adding predetermined amounts of an 18% by mass aqueous solution of sodium hydroxide to the gel composition obtained, and homogeneously stirring the mixtures. Then, the viscosities at various pHs of the neutral viscous solution were measured. The results are shown in Table 6.

TABLE 6

| Comparative Example 2 Polymer 2/Polyoxyethelene Lauryl Ether Content: 0.5% by mass | |
|---|---|
| pH | Viscosity [mPa · s] |
| 3.69 | 27,200 |
| 4.74 | 81,000 |
| 5.14 | 107,000 |
| 5.91 | 127,000 |
| 6.4 | 117,000 |
| 7.04 | 102,000 |
| 7.6 | 93,800 |
| 9.26 | 88,200 |
| 12.09 | 80,800 |

As is evident from the results shown in Tables 3 and 6, it is found that when the polymer 2 (a polymer having a high crosslinking degree, as compared to the polymer 1) is used as in Referential Example 2, because the viscosity before addition of the nonionic emulsifier (the emulsifier content: 0% by mass (Referential Example 2) in Table 3) is high in the wide pH range of about 4 to 12, the components are less readily homogeneously dispersed or dissolved than in Examples 5 and 6. Although the addition of the nonionic emulsifier to the polymer 2 (Comparative Example 2) increases the viscosity in the pH range of 4 to 12, the viscosity before addition of the nonionic emulsifier is excessively high, and thus, the gel composition is difficult to use.

The invention claimed is:

1. A gel composition comprising:
   0.5 to 1.5% by mass of a neutralized product of an alkyl-modified carboxyl group-containing polymer, which is a copolymer of monomers comprising 100 parts by mass of (meth)acrylic acid (a), 2.5 to 5 parts by mass of a (meth)acrylic acid alkyl ester (b) in which the alkyl group has 18 to 24 carbon atoms, and 0.1 part by mass or less of a compound (c) having two or more ethylenically unsaturated groups, and
   an anionic emulsifier,
   wherein a content of solids in the anionic emulsifier is 0.05 to 1% by mass, the composition has a pH of from 4 to 5.6, and the composition has a viscosity of from 15,000 mPa·s to 200,000 mPa·s.

2. The gel composition according to claim 1, wherein the compound (c) having two or more ethylenically unsaturated groups is at least one selected from the group consisting of pentaerythritol allyl ethers, diethylene glycol diallyl ether, polyethylene glycol diallyl ether, and polyallylsaccharose.

3. The gel composition according to claim 1, wherein the anionic emulsifier is an alkyl sulfate.

4. A cosmetic preparation comprising the gel composition according to claim 1.

5. A method for producing a gel composition comprising the steps of:

mixing an alkyl-modified carboxyl group-containing polymer, which is a copolymer of monomers comprising 100 parts by mass of (meth)acrylic acid (a), 2.5 to 5 parts by mass of a (meth)acrylic acid alkyl ester (b) in which the alkyl group has 18 to 24 carbon atoms, and 0.1 part by mass or less of a compound (c) having two or more ethylenically unsaturated groups, with an alkaline component, to prepare a neutralized product of the alkyl-modified carboxyl group-containing polymer; and mixing the neutralized product of the alkyl-modified carboxyl group-containing polymer with an anionic emulsifier, wherein a content of the neutralized product of an alkyl-modified carboxyl group-containing polymer in the gel composition is 0.5 to 1.5% by mass, and wherein a content of solids in the anionic emulsifier is 0.05 to 1% by mass, the composition has a pH of from 4 to 5.6, and the composition has a viscosity of from 15,000 mPa·s to 200,000 mPa·s.

6. A gel composition comprising:

0.5 to 1.5% by mass of a neutralized product of an alkyl-modified carboxyl group-containing polymer, which is a copolymer of monomers comprising 100 parts by mass of (meth)acrylic acid (a), 2.5 to 5 parts by mass of a (meth)acrylic acid alkyl ester (b) in which the alkyl group has 18 to 24 carbon atoms, and 0.1 part by mass or less of a compound (c) having two or more ethylenically unsaturated groups; and a nonionic emulsifier, wherein a content of solids in the nonionic emulsifier is 0.05 to 1% by mass, the composition has a pH of from 4 to 13, and the composition has a viscosity of from 20,000 mPa·s to 200,000 mPa·s.

7. The gel composition according to claim 6, wherein the compound (c) having two or more ethylenically unsaturated groups is at least one selected from the group consisting of pentaerythritol allyl ethers, diethylene glycol diallyl ether, polyethylene glycol diallyl ether, and polyallylsaccharose.

8. The gel composition according to claim 6, wherein the nonionic emulsifier is a polyoxyethylene alkyl ether.

9. A cosmetic preparation comprising the gel composition according to claim 1.

10. A method for producing a gel composition comprising the steps of:

mixing an alkyl-modified carboxyl group-containing polymer, which is a copolymer of monomers comprising 100 parts by mass of (meth)acrylic acid (a), 2.5 to 5 parts by mass of a (meth)acrylic acid alkyl ester (b) in which the alkyl group has 18 to 24 carbon atoms, and 0.1 part by mass or less of a compound (c) having two or more ethylenically unsaturated groups, with an alkaline component, to prepare a neutralized product of the alkyl-modified carboxyl group-containing polymer; and mixing the neutralized product of the alkyl-modified carboxyl group-containing polymer with a nonionic emulsifier, wherein a content of the neutralized product of an alkyl-modified carboxyl group-containing polymer in the gel composition is 0.5 to 1.5% by mass, a content of solids in the anionic emulsifier is 0.05 to 1% by mass, the composition has a pH of from 4 to 5.6, and the composition has a viscosity of from 15,000 mPa·s to 200,000 mPa·s.

\* \* \* \* \*